(12) United States Patent
Wong et al.

(10) Patent No.: US 7,661,641 B2
(45) Date of Patent: Feb. 16, 2010

(54) MEDICAL EQUIPMENT TRANSFER SYSTEM

(75) Inventors: Jean T. Y. Wong, Brossard (CA); Jonathan Levesque, Montreal (CA); Vincent Carbonneau Martel, Brossard (CA)

(73) Assignee: Linvatec Corporation, Largo, FL (US)

( * ) Notice: Subject to any disclaimer, the term of this patent is extended or adjusted under 35 U.S.C. 154(b) by 403 days.

(21) Appl. No.: 11/644,156

(22) Filed: Dec. 22, 2006

(65) Prior Publication Data

US 2008/0149788 A1    Jun. 26, 2008

(51) Int. Cl.
*E04G 3/00* (2006.01)

(52) U.S. Cl. .......................... 248/274.1; 5/600; 52/36.2; 248/343

(58) Field of Classification Search ............... 248/274.1, 248/291.1, 294.1, 289.11, 290.1, 317, 343, 248/311.3, 176.1; 5/600, 531, 658; 211/13; 52/36.2

See application file for complete search history.

(56) References Cited

U.S. PATENT DOCUMENTS

| | | | |
|---|---|---|---|
| 4,738,369 A | 4/1988 | Desjardins | |
| 5,117,521 A | 6/1992 | Foster et al. | |
| 5,236,162 A | 8/1993 | Desjardins | |
| 5,306,109 A | 4/1994 | Kreuzer et al. | |
| 5,513,406 A | 5/1996 | Foster et al. | |
| 5,527,125 A | 6/1996 | Kreuzer et al. | |
| 5,647,491 A | 7/1997 | Foster et al. | |
| 6,073,285 A | 6/2000 | Ambach et al. | |
| 6,089,518 A | 7/2000 | Nilsson | |
| 7,065,812 B2 * | 6/2006 | Newkirk et al. | 5/600 |
| 7,073,765 B2 * | 7/2006 | Newkirk | 248/647 |
| 7,219,472 B2 * | 5/2007 | Gallant et al. | 52/36.2 |
| 2004/0164220 A1 * | 8/2004 | Newkirk | 248/647 |
| 2006/0107026 A1 * | 5/2006 | Oh | 711/220 |
| 2006/0179571 A1 | 8/2006 | Newkirk | |
| 2006/0242763 A1 * | 11/2006 | Graham et al. | 5/503.1 |

OTHER PUBLICATIONS

Article Entitled "A Safer Way to Move Transtat. Device Transport System" by Steris Corporation Printed Jul. 2006.
Article Entitled "Transtat.. Device Transport System" by Steris Corporation Printed Jul. 1, 2006.

* cited by examiner

*Primary Examiner*—Ramon O Ramirez (57) ABSTRACT

The present invention provides a medical equipment transfer system in which the medical equipment is transferable between alternative support bases. In one aspect of the invention, the system includes first and second support bases and an equipment carriage. The equipment carriage defines a first locking assembly for selectively locking with the first support base and a second locking assembly for selectively locking with the second support base and is simultaneously engageable with the first and second support bases via the first and second locking assemblies. An actuator is operable to simultaneously unlock the equipment carriage from the first support base and lock the equipment carriage to the second support base.

14 Claims, 9 Drawing Sheets

MEDICAL EQUIPMENT TRANSFER SYSTEM

FIELD OF THE INVENTION

The invention relates to a medical equipment transfer system having a medical equipment carriage transferable between various support bases.

BACKGROUND

As patients progress through medical treatment, it is often necessary for the patient to move from room to room in a medical treatment facility and from one patient support device to another. For example, a surgical patient may move between a pre-surgical preparation area, an operating room, a post operative recovery area, and a patient recovery room. The patient may be transferred between a gurney, a surgical table, a hospital bed, and a wheel chair. During all of this movement, the patient may be connected to various items of medical equipment that must move with the patient through the medical treatment facility. Typically, such equipment is attached to a mobile base that allows it to be wheeled along beside the patient.

Some shortcomings of mobile bases are that they can be unwieldy to push along with the patient transport device and they can tip over causing injuries and equipment damage. Prior attempts at addressing these shortcomings include providing mobile bases that couple to a patient transport and trail along behind the patient transport. U.S. Pat. No. 4,945,592 discloses a wheeled bed and a separate wheeled equipment base. The equipment stand includes a horizontally extending flange with a downwardly extending pin that engages a socket mounted to the bed. As the bed is moved, the equipment stand is pulled behind. To uncouple the equipment base from the bed, the bed is lowered until the socket and pin are disengaged. U.S. Pat. No. 6,073,285 discloses a similar device with a wheeled equipment base hitched to a patient bed.

Another shortcoming of mobile bases is that they take up space and can get in the way of personnel and other necessary equipment. Prior solutions to this shortcoming include providing equipment stands that can be selectively coupled to a patient transport and to a fixed support base in a patient treatment room. Fixed support bases can take the form of ceiling mounted service arms, floor mounted columns, and wall mounted headwalls. For example U.S. Pat. No. 7,065,812 discloses an equipment support that can be selectively mounted to an arm extending from a wall, on a column depending from the arm, on a wall mount, on a stand, or on a patient support. For example, the equipment support can be transferred from a free standing floor stand, to a rail on a patient bed, to a ceiling mounted arm. The equipment support includes a pair of parallel spikes extending downwardly from the bottom of the support to engage an upwardly opening socket mounted on each of the various bases. The equipment support is transferred by engaging a subsequent base with an unused one of the parallel spikes and then vertically displacing the support from the prior base. U.S. Pat. No. 5,527,125 and U.S. Pat. No. 5,306,109 disclose a similar mechanism except that the equipment support includes a pair of parallel, conical, vertical openings that engage conical spikes on the various bases. The spikes include grooves and the openings include spring loaded plates that lock into the grooves to secure the spikes in the openings. When only a single spike is engaged with one of the openings, it is locked in place by one of the spring loaded plates. When the parallel openings are simultaneously engaged by a spike in each opening, such as when the equipment support is in process of being transferred from one base to another, both spikes are unlocked. The presence or absence of a spike in an adjacent opening determines whether a spike is unlocked or locked. All of these solutions include horizontally spaced locking mechanisms.

SUMMARY

The present invention provides a medical equipment transfer system in which the medical equipment is transferable between alternative support bases.

In one aspect of the invention, the system includes first and second support bases and an equipment carriage. The equipment carriage defines a first locking assembly with the first support base and a second locking assembly with the second support base and is simultaneously engageable with the first and second support bases via the first and second locking assemblies. An actuator is operable to simultaneously unlock the equipment carriage from the first support base and lock the equipment carriage to the second support base.

In another aspect of the invention, the first and second locking assemblies each include a locking ball and a ball pressing member. An elongated link is operable to move the ball pressing members between a locked and an unlocked position.

In another aspect of the invention, the medical equipment transfer system includes a safety mechanism operable to prevent the carriage from being unlocked from the first base unless the second base is engaged via the second locking assembly.

In another aspect of the invention, the medical equipment transfer system includes a separate safety release tool. The safety release tool is engageable with the safety mechanism to manually override the safety mechanism.

In another aspect of the invention, the equipment carriage further includes at least one service outlet mounted to the equipment carriage. The service outlet communicates with a connector to connect the service outlet to a service supply mounted to the first base when the first locking assembly is engaged.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Embodiments of a medical equipment transfer system include a support base and an equipment carriage. A support base may include a stand, tripod, cart, bed, wheel chair, gurney, surgical table, ceiling mounted service arm, floor mounted column, wall mounted headwall, and/or any other suitable base. Equipment may include intravenous infusion tubing, pumps, reservoirs, monitors, electrocardiogram machines, lights, anesthesia devices, and/or any other equipment for treating, diagnosing, monitoring, and/or otherwise interacting with a patient. The carriage may include service distribution outlets for electrical, vacuum, gas, water, and/or other services.

The carriage and bases may define locking assemblies. The carriage may include portions of two locking assemblies. The portions may be simultaneously engageable, in a non-locking manner, with different bases. The locking assemblies may be simultaneously actuable to simultaneously unlock from one base and lock to another base. The locking assemblies may be actuable by rotating, pivoting, sliding, rocking, pushing, pulling, and/or otherwise actuating the assemblies. The locking assemblies may be positioned close together, spaced far apart, positioned for parallel engagement, and/or positioned for coaxial engagement. For example, the locking assemblies may be positioned at opposite ends of the equipment carriage in coaxial alignment for simultaneous axial engagement with two support bases. Further for example, the locking assemblies may be responsive to an axially translatable actuator to simultaneously unlock one locking assembly while locking the other.

The equipment transfer system may include a safety mechanism that prevents the carriage from being unlocked from one base until another base is properly positioned for the carriage to lock to simultaneously with the unlocking.

Figure 1:
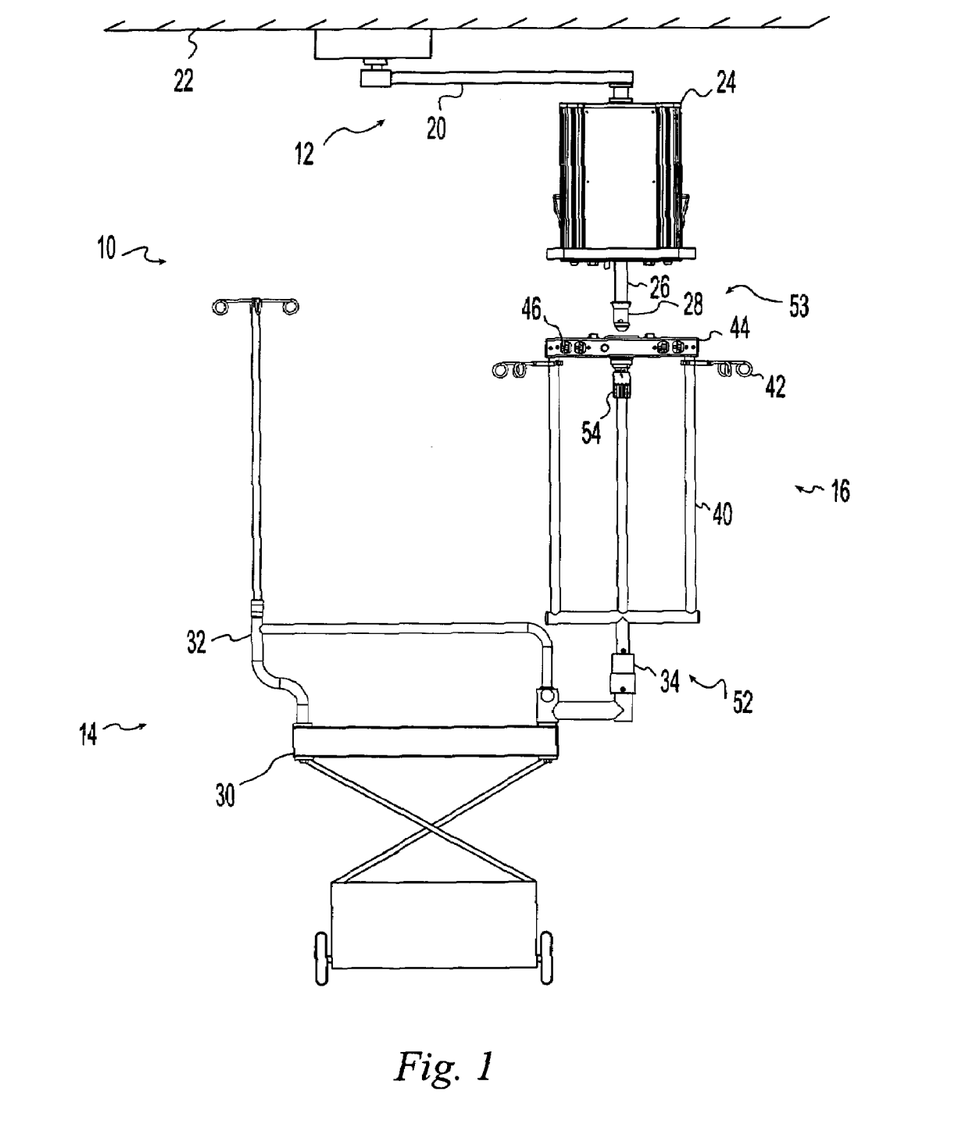
FIG. 1 is an elevation view of a medical equipment transfer system according to the present invention.
Figure 2:
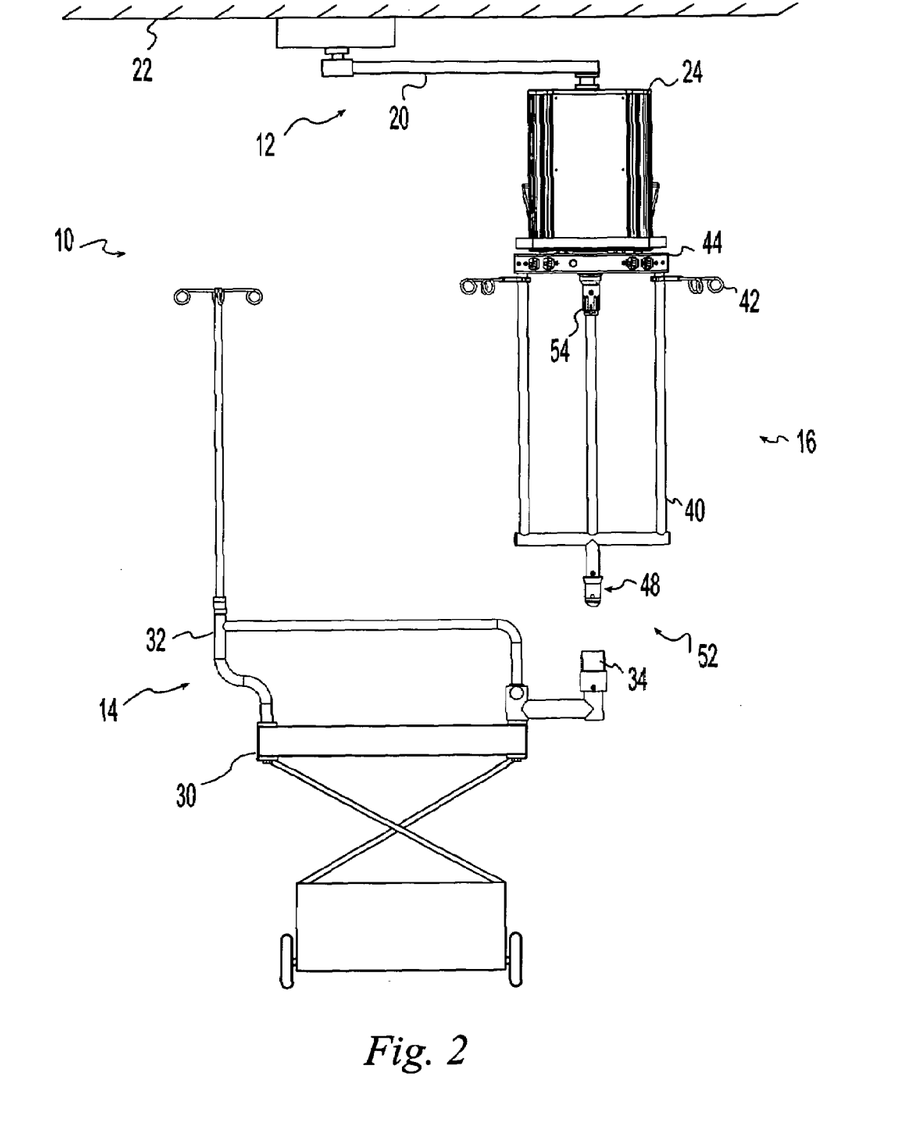
FIG. 2 is an elevation view of the medical equipment transfer system of FIG. 1.

FIGS. 1-10 depict an illustrative equipment transfer system 10 including a fixed base 12 and a mobile base 14. An equipment carriage 16 is transferable between the fixed base 12 and the mobile base 14. FIG. 1 illustrates the equipment carriage 16 locked to the mobile base 14 and FIG. 2 illustrates the equipment carriage 16 locked to the fixed base 12.

The illustrative fixed base 12 includes a service arm 20 mounted to the ceiling 22 and a service manager 24 suspended from the service arm 20. The service manager 24 includes an extendable piston 26 that can be driven between an extended position (FIG. 1) and a retracted position (FIG. 2). The piston 26 includes a male end fitting, or service manager plug 28. The service manager 24 may include electrical, water, gas and other utility supplies as well as house various patient monitoring and treatment equipment. The service arm 20 allows the service manager to 24 be moved while maintaining the utility supplies and other equipment in a nonintrusive yet easily accessed position.

The mobile base 14 includes a wheeled patient transport 30 and a support frame 32 mounted to it. The support frame includes an upwardly opening socket 34. The illustrative mobile base facilitates moving a patient through a medical treatment facility.

The equipment carriage 16 includes a rigid tubular frame 40 and hooks 42 for supporting equipment. For example, pumps (not shown) can be clamped to the frame 40 and fluid containers (not shown) can be hung from the hooks 42. The carriage 16 also includes a header 44 containing service outlets. The illustrative header 44 includes electrical outlets 46 that are electrically connected to the service manager 24 by connectors 47 (FIG. 3) mounted to the top of the header 44. The header 44 includes an indicator light 49 that lights when the connectors 47 are connected to the service manager 24. The carriage 16 includes a male end fitting, or carriage plug 48, extending downwardly from the frame 40 and a socket 50 extending into the header 44.

In use, the carriage 16 is transferred with the patient to maintain a continuous connection between the patient and the medical equipment mounted to the carriage. For example, the carriage 16 is mounted to the support frame 32 by inserting the carriage plug 48 into the support frame socket 34. The carriage plug 48 and support frame socket 34 define a lower lock assembly 52 the function of which will be more fully explained below. A patient is prepared for surgery in a pre-operative preparation room by connecting the patient to various pieces of equipment. The equipment is mounted to the carriage 16. The patient is conveyed to the operating room on the patient transport 30 accompanied by the connected equipment supported on the support frame 32. Once in the operating room, the patient is transferred to an operating table and the carriage 16 is transferred to the service manager 24. The carriage 16 is transferred by lowering the piston 26 (FIG. 1) to engage the service manager plug 28 with the carriage socket 50. The service manager plug 28 and carriage socket 50 define an upper lock assembly 53. An actuator sleeve 54 is operable to simultaneously move the lower lock assembly 52 and upper lock assembly 53 between locked and unlocked positions. The lower lock assembly 52 is in the locked position when the upper lock assembly 53 is in the unlocked position. In the illustrative embodiment, this condition is referred to as the "bed locked" position. The lower lock assembly 52 is in the unlocked position when the upper lock assembly 53 is in the locked position. In the illustrative embodiment, this condition is referred to as the "arm locked" position. With the lock assemblies in the "arm locked" position (FIG. 2), the piston 26 is retracted into the service manager 24 to raise the carriage 16 and support it adjacent the patient. The patient transport 30 is then removed from the operation room. After surgery is completed, the patient transport 30 is brought back into position beside the operating table, the patient is transferred back to the transport, and the carriage 16 is transferred back to the support frame 32 by reversing the above steps. The patient is conveyed to a recovery room on the transport 30 accompanied by the connected equipment. The illustrative medical equipment transfer system 10 thus enables the patient to remain connected to medical equipment throughout preparation, surgery, and recovery while obviating the need for additional equipment carts.

Figure 3A:
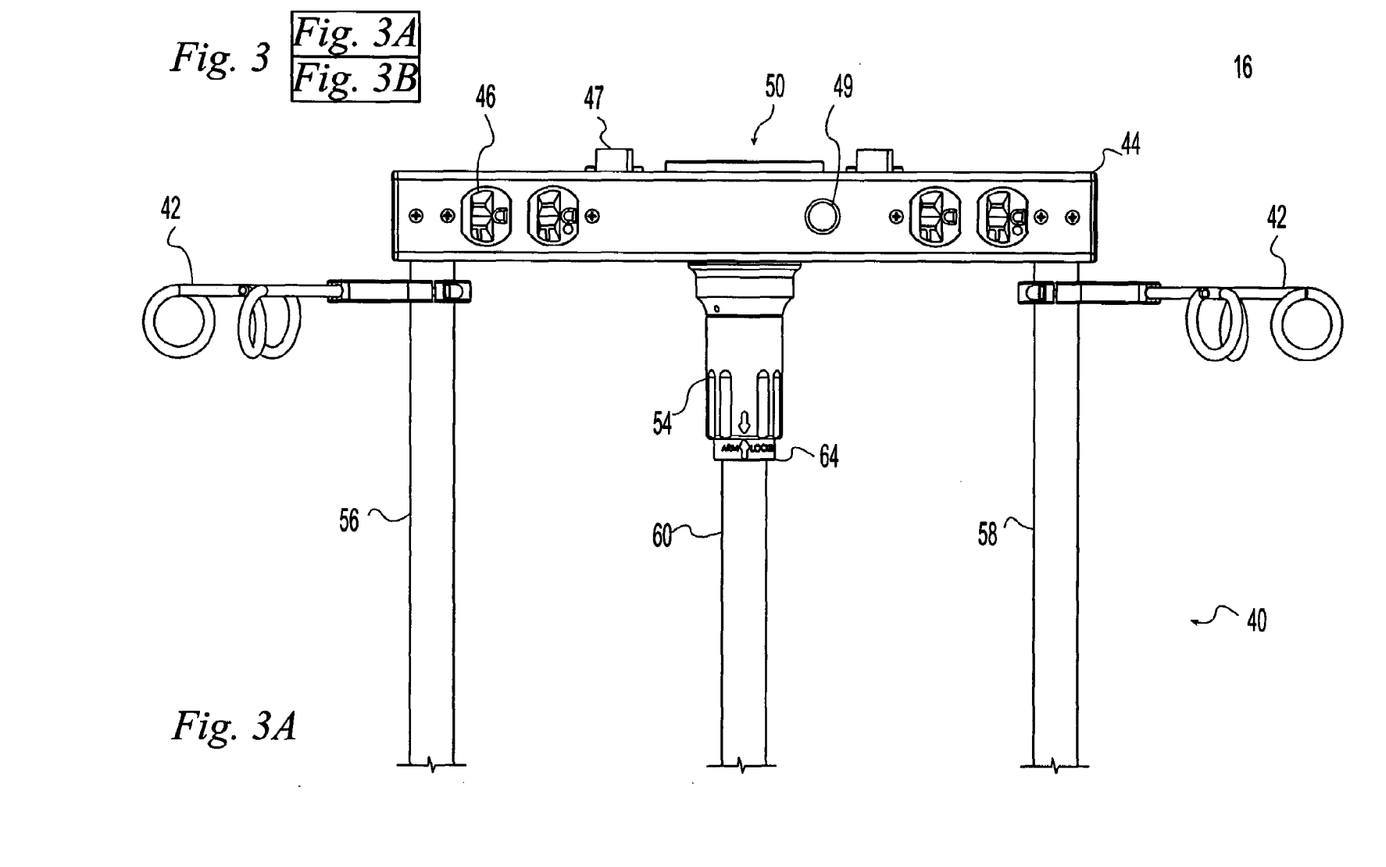
FIG. 3 is an elevation view of the carriage component of the medical equipment transfer system of FIG. 1.
Figures 3B, 4:
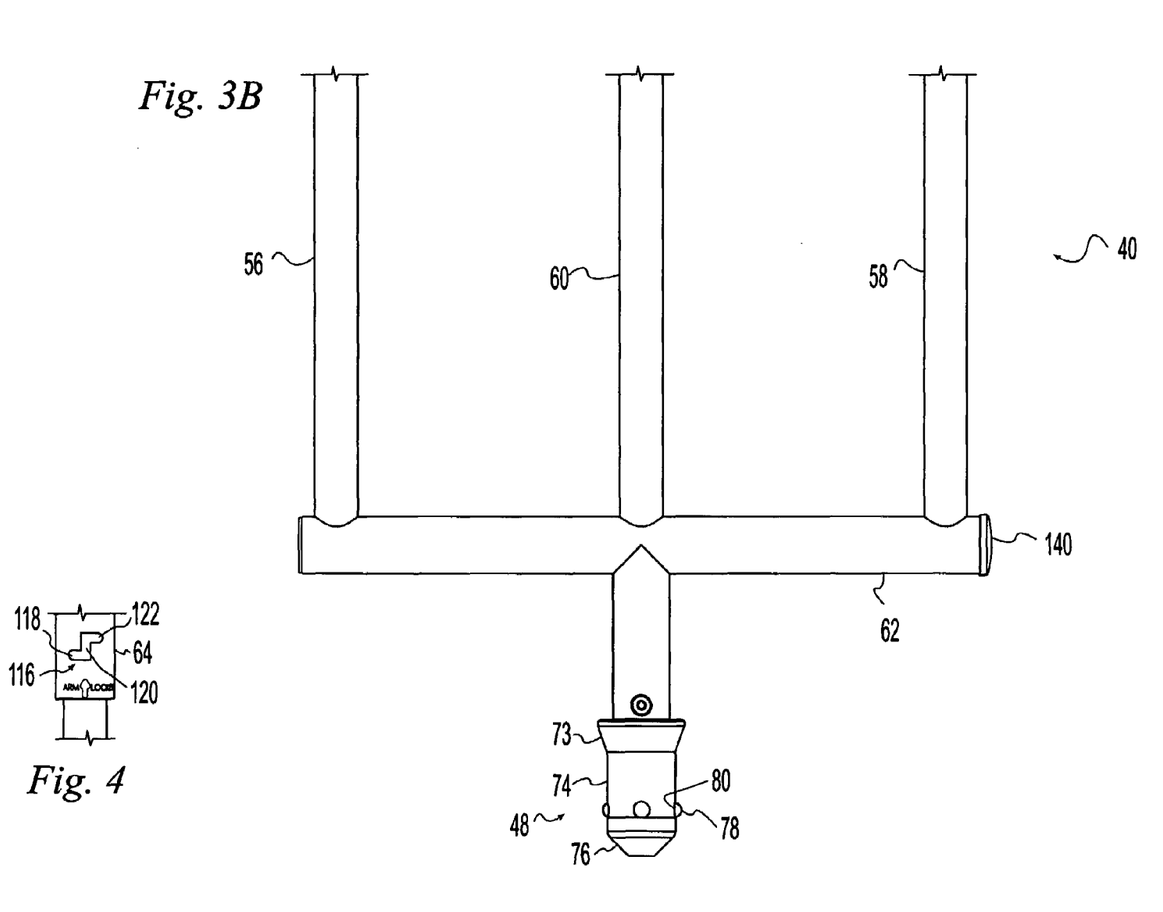
FIG. 4 is a detail view of the sleeve slot of the carriage component of the medical equipment transfer system of FIG. 1.

FIGS. 3-10 depict the mechanical details of the medical equipment transfer system 10. Referring to FIG. 3, the carriage frame 40 includes three vertical tubes 56, 58, and 60 connected at the top to the header 44 and at the bottom to a horizontal tube 62. The upper end of the central tube 60 is mounted to a sleeve 64 which in turn is mounted to the header 44. The sleeve 64 defines the carriage socket 50 including an inner bore (FIG. 7) having an inwardly tapering seat 67, a generally cylindrical main bore 68, and an inwardly tapering lower portion 70. The main bore 68 is divided by an annular inwardly projecting shoulder 72. The sleeve 64 houses an upper carriage locking mechanism.

Referring to FIG. 3B, the lower end of the central tube 60 extends below the horizontal frame tube 62 and is connected to the carriage plug 48. The carriage plug 48 includes an inwardly tapering flange 73, a generally cylindrical plug body 74 and an inwardly tapering tip 76. An axial through bore 77 (FIG. 6) communicates through the tip 76 to communicate from the exterior of the plug 48 to the interior of the plug 48. The plug 48 houses a lower carriage locking mechanism.

The upper and lower carriage locking mechanisms are linked by an actuator tube 82 (FIG. 5) coaxially mounted for axial translation within the central tube 60. As the actuator tube 82 translates upwardly it actuates the upper and lower lock assemblies 53, 52 to position them in the "arm locked" position. As the actuator tube 82 translates downwardly, it actuates the upper and lower lock assemblies 53, 52 to position them in the "bed locked" position.

Figure 6:
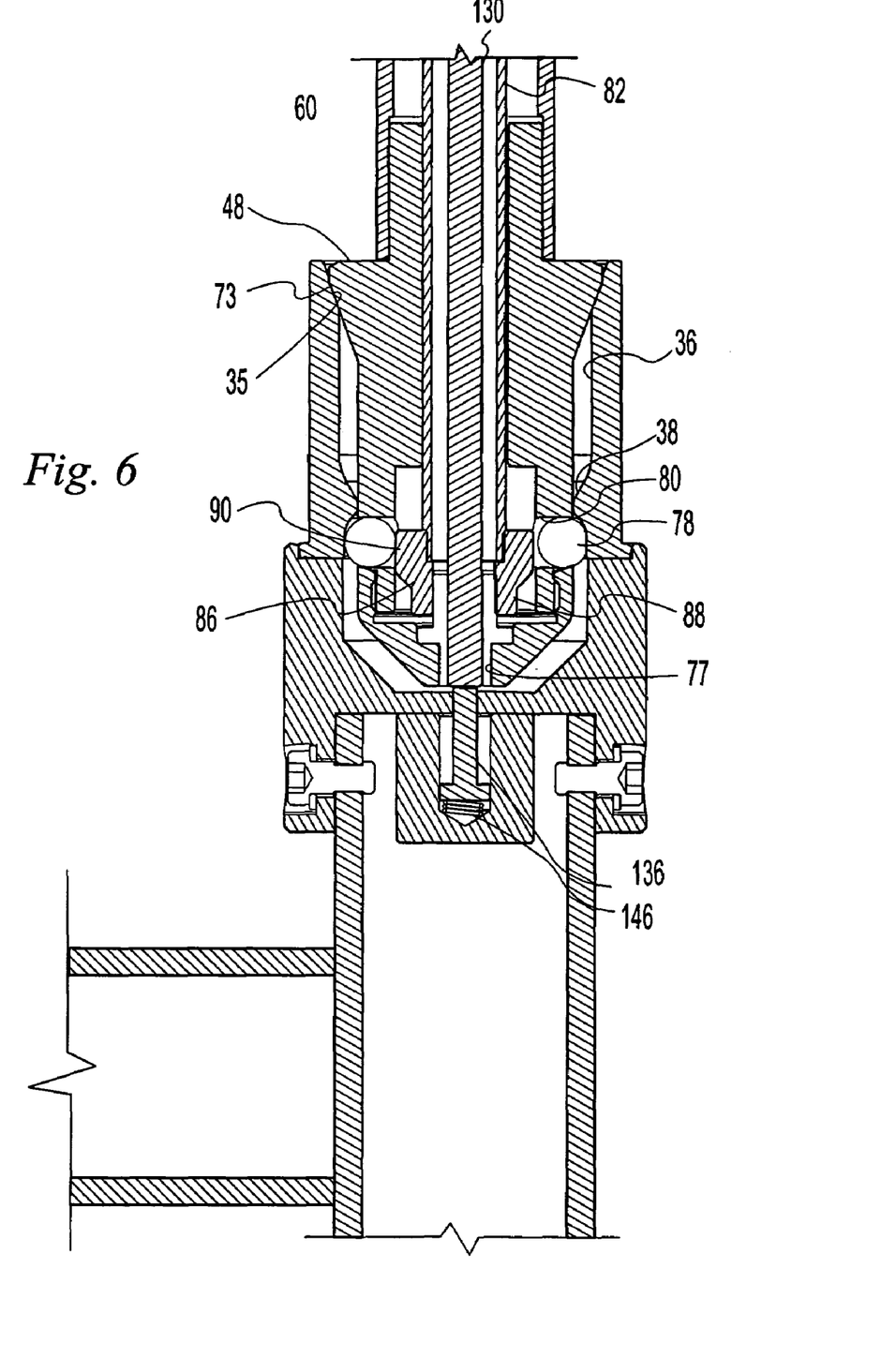
FIG. 6 is a cross-sectional view of the lower lock assembly of the medical equipment transfer system of FIG. 1 in the locked position.
Figures 8, 10:
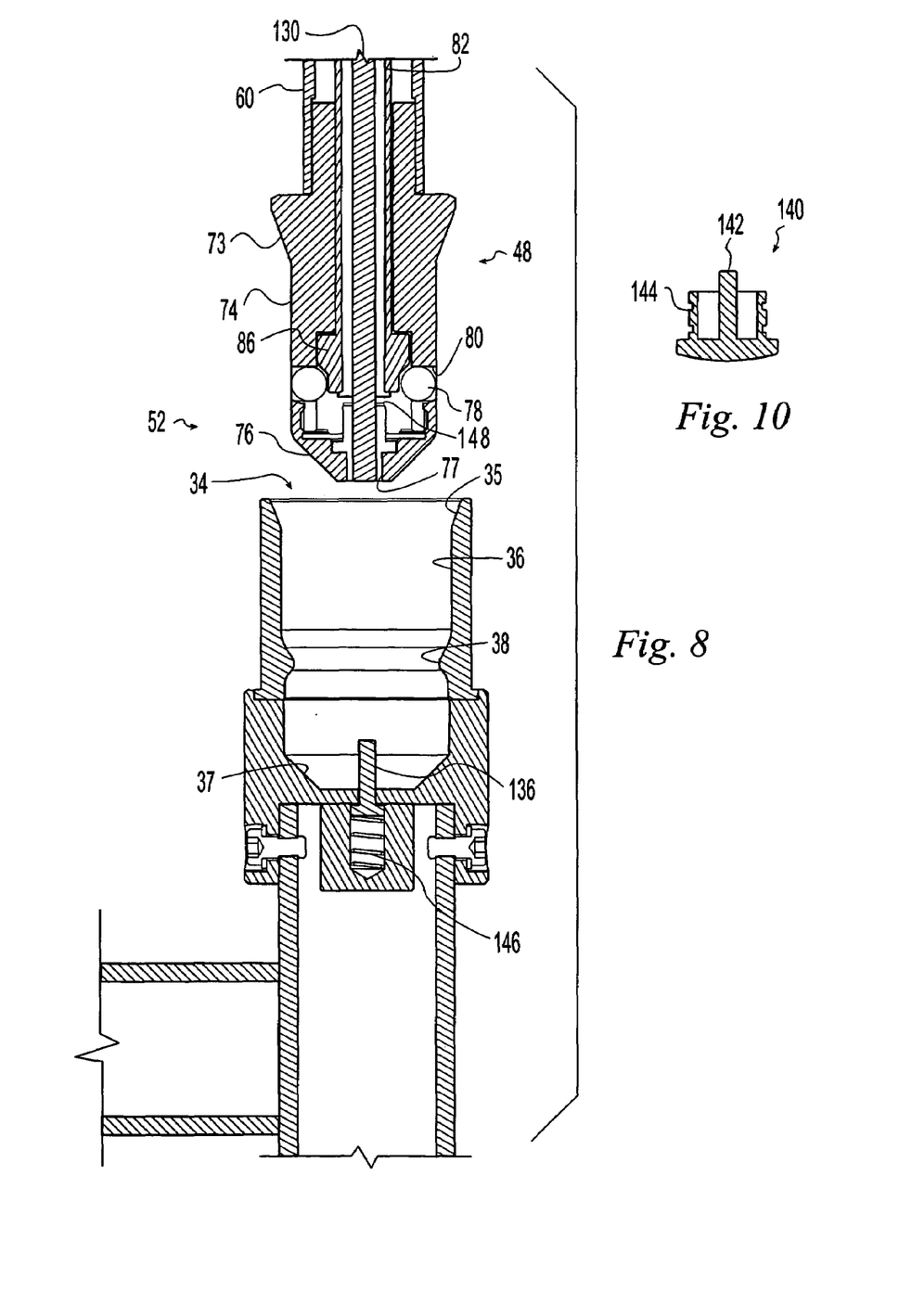
FIG. 8 is a cross-sectional view of the lower lock assembly of the medical equipment transfer system of FIG. 1 in the unlocked position.
FIG. 10 is a cross-sectional view of a safety tool component of the medical equipment transfer system of FIG. 1.

FIG. 6 illustrates the lower lock assembly 52 in the "bed locked" position. FIG. 8 illustrates the lower lock assembly 52 in the arm locked position. The lower lock assembly 52 includes the carriage plug 48 and the support frame socket 34. The support frame socket 34 includes an inwardly tapering seat 35, a generally cylindrical main bore 36, and an inwardly tapering lower portion 37. The main bore 36 is divided by an annular inwardly projecting shoulder 38. The carriage plug 48 includes locking balls 78 mounted in the carriage plug 48 for radial translation between a locked position (FIG. 6) and an unlocked position (FIG. 8). In the locked position, the locking balls 78 are pressed radially outwardly to project beyond the outer surface of the cylindrical plug body 74 through holes 80. In the unlocked position, the locking balls 78 are free to translate radially inwardly. A lower locking cone 86 is connected to the lower end of the actuator tube 82 in axial force transmitting relationship. The lower locking cone 86 tapers from a lower narrower portion 88 and an upper wider portion 90. As the actuator tube 82 translates downwardly, the wider portion 90 of the lower locking cone 86 presses the locking balls 78 radially outwardly (FIG. 6). To lock the carriage 16 to the support frame 32, the carriage plug 48 is inserted into the support frame socket 34 until the tapered flange 73 rests on the seat 35. The actuator tube 82 is then moved downwardly to force the locking balls 78 outwardly to engage the lower side of the shoulder 38. With the balls 78 engaged with the shoulder 38, the plug 48 is locked in the socket 34. To unlock the carriage 16 from the support frame 32, the actuator tube 82 and lower locking cone 86 are moved upwardly to allow the balls 78 to translate radially inwardly, thus freeing the plug 48 to be removed upwardly out of the socket 34.

Figure 7:
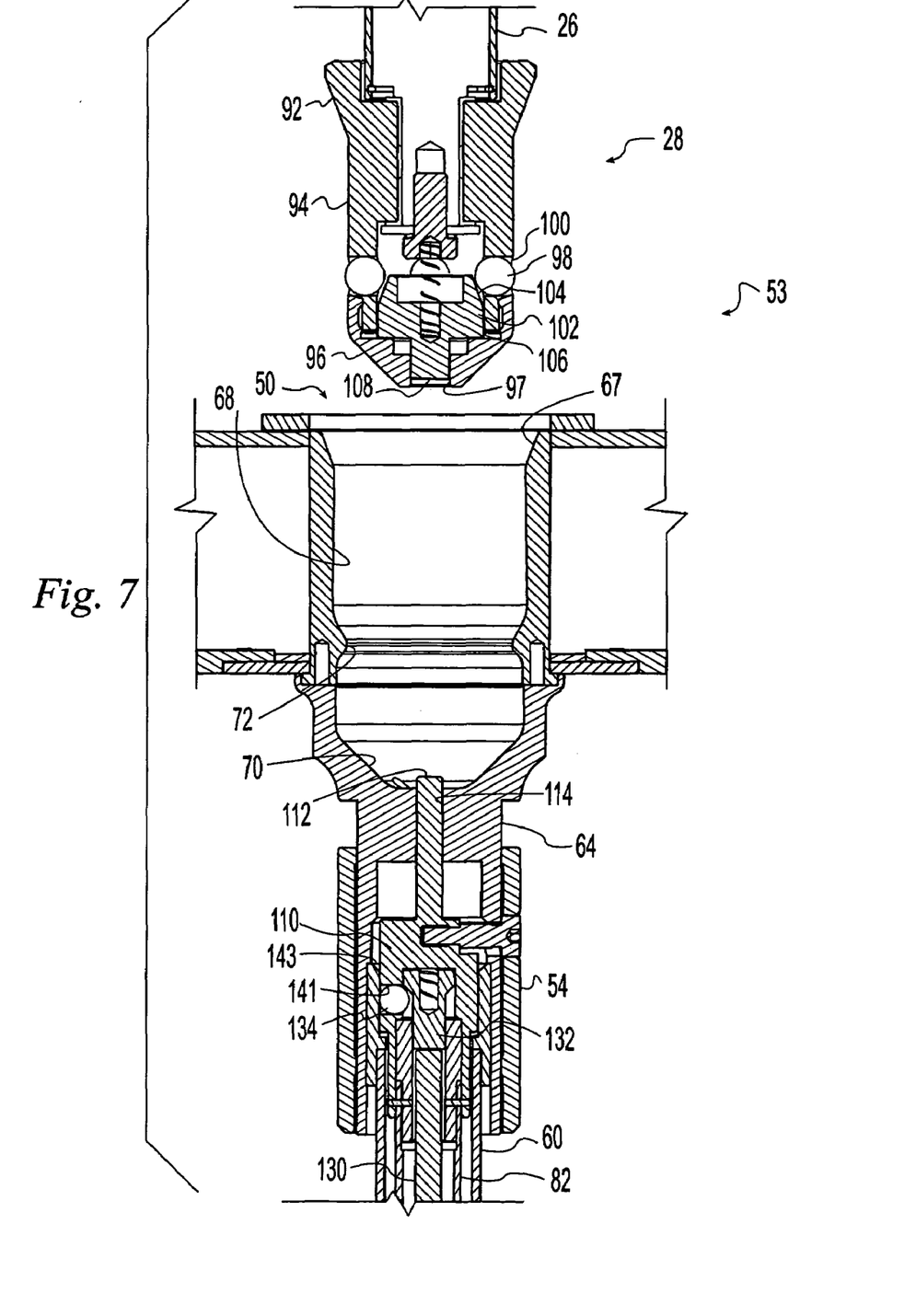
FIG. 7 is a cross-sectional view of the upper lock assembly of the medical equipment transfer system of FIG. 1 in the unlocked position.
Figure 9:
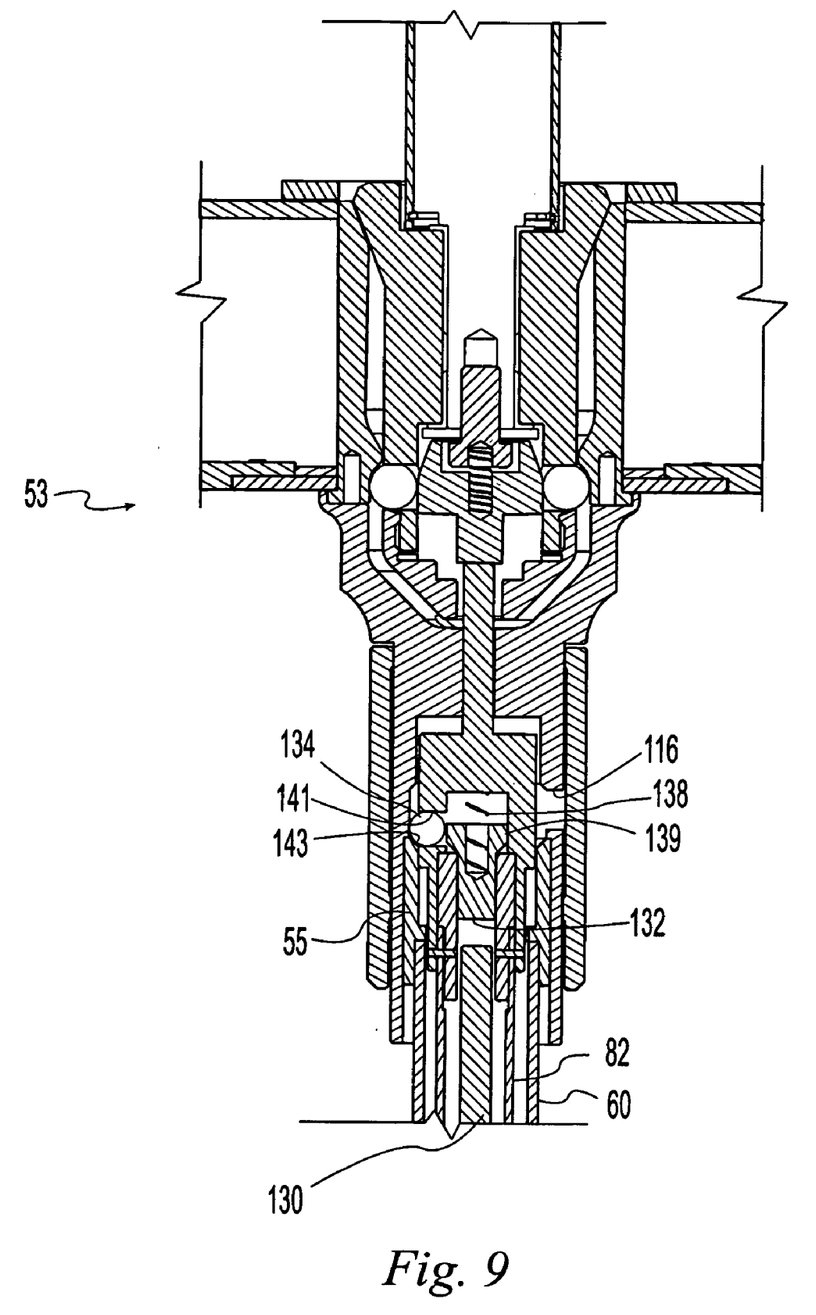
FIG. 9 is a cross-sectional view of the upper lock assembly of the medical equipment transfer system of FIG. 1 in the locked position.

FIG. 7 illustrates the upper lock assembly 53 in the "bed locked" position. FIG. 9 illustrates the upper lock assembly in the "arm locked" position. The upper lock assembly 53 includes the service manager plug 28 and the carriage socket 50. The service manager plug 28 includes an inwardly tapering flange 92, a generally cylindrical plug body 94, and an inwardly tapering tip 96. A throughbore 97 in the tip 96 communicates from the exterior to the interior of the service manager plug 28. The service manager plug 28 houses a locking mechanism including locking balls 98 mounted in the service manager plug 28 for radial translation between a locked position (FIG. 9) and an unlocked position (FIG. 7). In the locked position, the locking balls 98 are pressed radially outwardly to project beyond the outer surface of the cylindrical plug body 94 through holes 100. In the unlocked position, the locking balls 98 are free to translate radially inwardly. An upper locking cone 102 is mounted in the service manager plug 28 for axial translation. The upper locking cone 102 tapers from an upper narrower portion 104 to a lower wider portion 106. A cylindrical post 108 extends downwardly from the lower portion 106 and is received in the throughbore 97 for axial translation. As the upper locking cone 102 is pressed upwardly, the wider portion 106 presses the locking balls 98 radially outwardly (FIG. 9).

Figure 5:
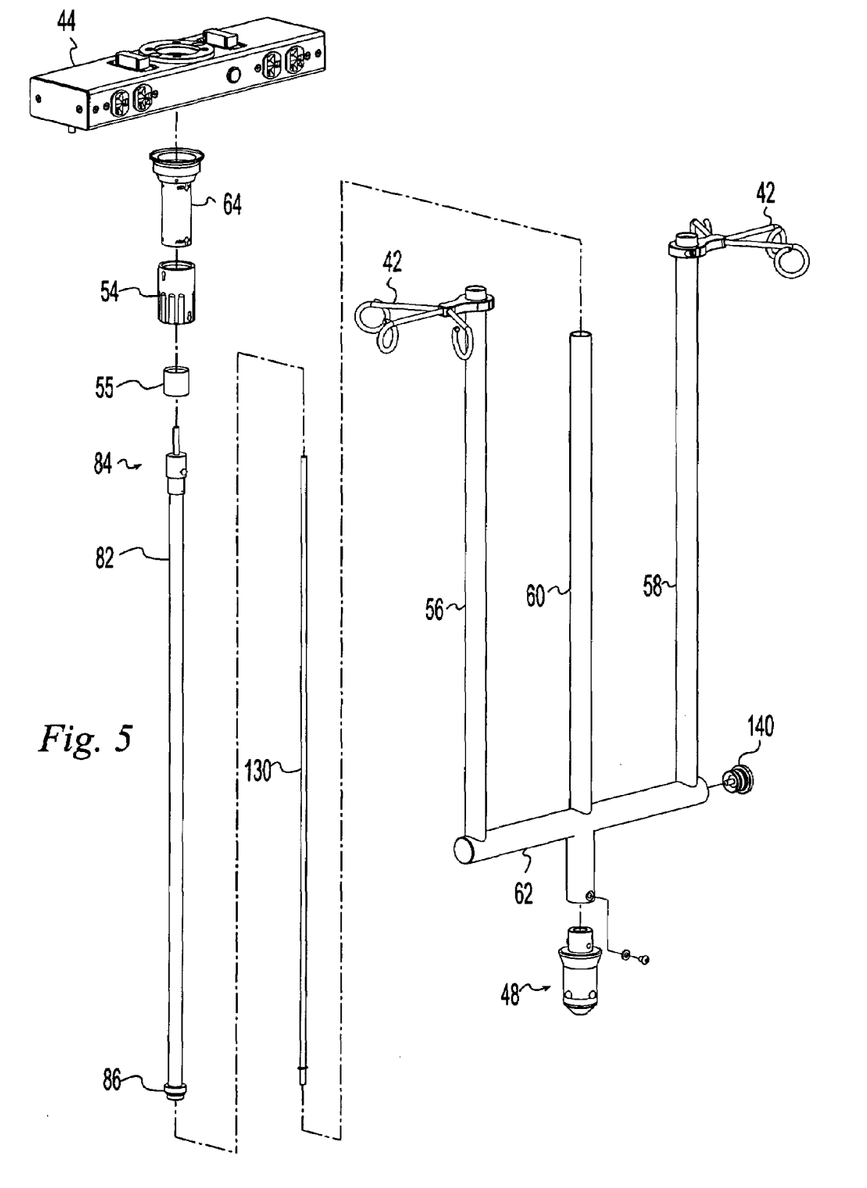
FIG. 5 is an exploded perspective view of the carriage component of the medical equipment transfer system of FIG. 1.

The upper locking cone 102 is pressed upwardly by the upper lock actuator assembly 84 (FIG. 5). The upper lock actuator assembly 84 includes an actuator 110 mounted for axial translation in the sleeve 64 of the carriage 16. An elongated cylindrical actuator tip 112 projects upwardly from the actuator 110 and is received for axial translation in a throughbore 114 communicating from the sleeve interior to the carriage socket 50. The actuator 110 is movable between a locked position (FIG. 9) and an unlocked position (FIG. 7). The actuator 110 is connected to the upper end of the actuator tube 82 in axial force transmitting relationship. As the actuator tube 82 is moved upwardly, it drives the actuator 110 upwardly and extends the actuator tip 112 into the throughbore 97 in the service manager plug 28 where it presses the upper locking cone 102 upwardly into the locked position (FIG. 9).

To lock the carriage 16 to the service manager 24, the service manager piston 26 is extended to lower the service manager plug 28 into the carriage socket 50 until the tapered flange 92 rests on the seat 67. The actuator tube 82 is then moved upwardly to press the actuator tip 112 against the upper locking cone 102 to drive it upwardly. The upper locking cone 102 forces the locking balls 98 outwardly to engage the lower side of the shoulder 72. With the balls 98 engaged with the shoulder 72, the plug 28 is locked in the socket 50. To unlock the carriage 16 from the service manager 24, the actuator tube 82 is moved downwardly to allow the balls 98 to translate radially inwardly, thus freeing the plug 28 to be removed upwardly out of the socket 50.

The actuator sleeve 54 (FIG. 3) is mounted coaxially on the outside of the carriage sleeve 64 and is pinned to the actuator 110 through a "Z"-shaped slot 116 (FIG. 4). The actuator sleeve 54 is rotatable about its longitudinal axis from a "bed locked" position 118 corresponding to a lower horizontal portion of the "Z"-shaped slot 116, to a neutral position 120 corresponding to a vertical portion of the "Z"-shaped slot 116, to an "arm locked" position 122 corresponding to an upper horizontal portion of the "Z"-shaped slot 116. In the neutral position 120, the actuator sleeve 54 is translatable up and down between the "bed locked" and "arm locked" positions and drives the actuator 110 and actuator tube 82 up and down with it. By rotating the actuator sleeve 54 into the "bed locked" or "arm locked" positions 118, 122, it is prevented from being inadvertently translated up and down.

The illustrative carriage 16 includes a safety mechanism to prevent the carriage from being released from the service manager plug 28 unless the carriage plug 48 is engaged with the support frame socket 34. The safety mechanism includes a safety rod 130 extending from the lower locking assembly to the upper locking assembly, a safety cone 132 and corresponding actuator locking ball 134 mounted in the upper locking assembly (FIGS. 7 and 9), and a safety release pin 136 mounted in the support frame socket 34 (FIGS. 6 and 8). In the "arm locked" position (FIGS. 8 and 9) the safety cone 132 (FIG. 9) is biased downwardly by safety cone spring 138 causing an enlarged upper portion 139 of the safety cone 132 to press the locking ball 134 radially outwardly to extend through a bore 141 in the actuator 110. The locking ball 134 abuts a shoulder 143 in the bushing 55 and prevents the actuator 110 from moving downwardly to the bed locked position.

The only way for the actuator 110 to be released to move to the "bed locked" position is for the safety cone 132 to be raised against the safety cone spring 138 to move the upper portion 139 of the safety cone 132 out of engagement with the locking ball 134 and permit the locking ball 134 to translate radially inwardly. The safety rod 130 raises the safety cone 132 when the carriage plug 48 is fully engaged in the support frame socket 34. The safety release pin 136 (FIG. 8) is biased upwardly by a safety release spring 146 so that the safety release pin 136 projects into the support frame socket 34. When the carriage plug 48 is engaged with the support frame socket 34, the safety release pin 136 extends through the bore 77 in the tip 76 of the carriage plug 48 and presses the safety rod 130 upwardly. The safety rod 130 in turn presses the safety cone 132 upwardly to enable the actuator 110 to be moved between the "arm locked" and "bed locked" positions. A retaining clip 148 (FIG. 8) prevents the safety rod 130 from falling out of the carriage 16 when it is in the "arm locked" position.

When the actuator 110 is in the "bed locked" position (FIG. 7), the locking ball 134 and safety cone 132 are below the shoulder 143 and the locking ball is prevented from engaging the shoulder 143. Therefore, the actuator is free to move upwardly to the frame locked position.

There may be times when the safety mechanism needs to be overridden. For example, in an emergency, a carriage 16 attached to the service manager 24 may have to be moved without a support frame to receive it. A safety tool 140 (FIG. 10) is provided for manually raising the safety rod 130. The safety tool 140 includes a release pin 142 that can be inserted through the bore 77 in the carriage plug 48 tip 76 to raise the safety rod 130 and enable the actuator 110 to be moved to the bed locked position. The safety tool 140 includes a body 144 in the shape of an end plug for the horizontal tube 62 of the frame 40 (FIG. 3B). The safety tool 140 is stored by pressing it into the end of the horizontal tube 62 where it is readily available in an emergency.

The illustrative medical equipment transfer system allows a medical equipment carriage to be securely and releasably locked to a first support base and easily and safely transferred to a second support base. The locking mechanism provides simultaneous unlocking of the carriage from the first support base and locking of the carriage to the second support base such that the carriage is always locked to one of the two bases and there is no intermediate step in which the carriage is unlocked from both support bases. The simultaneous unlocking and locking is driven by a single motion of an actuator making the transfer quick and simple. The system includes axially aligned locking mechanisms that require no horizontal offset from one another and thus enable the equipment carriage to be configured in a narrow and unobtrusive way.

Although examples of a medical equipment transfer system and its use have been described and illustrated in detail, it is to be understood that the same is intended by way of illustration and example only and is not to be taken by way of limitation. The illustrative medical equipment transfer system has been described in use to transfer intravenous infusion equipment from a wheeled patient bed to a service arm assembly in an operating room. However, the system can be used to mount any kind of equipment and transfer it between any kind of support bases. Likewise, the illustrative carriage has been shown with a frame including three vertical tubular members to which equipment can be attached. However, the carriage can be configured in any suitable shape and made of any suitable material. The carriage can be as simple as a single narrow member and a pair of locking assemblies or as elaborate as a multi-shelf unit designed to hold various pieces of equipment and provide a wide variety of service outlets. Similarly, the illustrative system has been shown with particular male and female members engageable in various locking and safety mechanisms. It will be readily apparent that the male/female relationships may be reversed in many cases and the illustrative system will still remain functional. Finally, the illustrative system has been illustrated in use to facilitate the transfer of a patient through a surgical facility. However, the system may be used in any environment including hospitals, clinics, nursing facilities, homes, and public areas. Accordingly, variations in and modifications to the medical equipment transfer system and its use will be apparent to those of ordinary skill in the art, and the following claims are intended to cover all such modifications and equivalents.

What is claimed is:

1. A medical equipment transfer system, comprising:
    a first support base;
    a second support base;
    an equipment carriage, the equipment carriage defining a first locking assembly and a second locking assembly, the first locking assembly being operative to secure the equipment carriage to the first support base to prevent it from being removed from the first support base in a locked position and permit it to be removed when it is in an unlocked position, the second locking assembly being operative to secure the equipment carriage to the second support base to prevent it from being removed from the second support base when it is in a locked position and permit it to be removed when it is in an unlocked position, the equipment carriage being simultaneously engageable with the first and second support bases via the first and second locking assemblies; and
    an actuator operable to simultaneously unlock the equipment carriage from one of the first and second support bases and lock the equipment carriage to the other base, i.e. the second or first support base, respectively.

2. The medical equipment transfer system of claim 1 wherein the equipment carriage comprises an elongated axial assembly, the first and second locking assemblies being simultaneously axially engageable with the first and second support bases, the equipment carriage defining a first portion of the first locking assembly at a first end of the carriage and defining a second portion of the second locking assembly at a second, axial opposed end.

3. The medical equipment transfer system of claim 2 wherein the equipment carriage further comprises an elongated link mounted to the equipment carriage for axial translation, the elongated link connecting the first and second portions, the actuator being mounted to the equipment carriage for axial translation and being operable to move the link to operate the first and second locking assemblies.

4. The medical equipment transfer system of claim 3 wherein the first and second locking assemblies each comprise a locking ball mounted for inward and outward radial translation and a ball pressing member mounted for axial translation adjacent to the locking ball, each ball pressing member being translatable between a locked position in which it presses a locking ball radially and an unlocked position in which it permits free radial movement of the ball, the elongated link being operable to move the ball pressing members between the locked and unlocked positions.

5. The medical equipment transfer system of claim 1 further comprising a safety mechanism operable to prevent the carriage from being unlocked from the first support base unless the second support base is engaged via the second locking assembly.

6. The medical equipment transfer system of claim 5 wherein the safety mechanism comprises an elongated safety link mounted to the equipment carriage for axial translation, the link being responsive to the absence of the second base engagement with the equipment carriage to prevent the actuator from moving to unlock the first locking assembly, the safety link being responsive to the presence of the second base engagement with the equipment carriage to permit the actuator to move to unlock the first locking assembly.

7. The medical equipment transfer system of claim 6 wherein the safety mechanism comprises a safety locking ball mounted for inward and outward radial translation and a safety ball pressing member mounted for axial translation adjacent to the locking ball, the safety ball pressing member being translatable between a locked position in which it presses the safety ball radially to block movement of the actuator in a direction that would unlock the first locking assembly and an unlocked position in which it permits the safety ball to move radially away from blocking the actuator, the elongated safety link being operable to move the safety ball pressing member to the unlocked position.

8. The medical equipment transfer system of claim 7 wherein the second support base includes a safety release pin, the safety release pin pressing the elongated safety link to translate it axially when the equipment carriage is engaged with the second support base to move the safety ball pressing member to the unlocked position.

9. The medical equipment transfer system of claim 7 further comprising a separate safety release tool, the safety release tool comprising a body and an elongated pin extending from the body, the elongated pin being engageable with the safety link to manually translate the safety link axially when the equipment carriage is disengaged from the second support base to override the safety mechanism.

10. The medical equipment transfer system of claim 1 wherein the first and second support bases are selected from the group consisting of stands, tripods, cart, beds, wheelchairs, gurneys, surgical tables, ceiling mounted service arms, floor mounted columns, and wall mounted headwalls.

11. The medical equipment transfer system of claim 1 further comprising at least one piece of equipment mounted to the equipment carriage, the at least one piece of equipment being selected from the group consisting of intravenous infusion tubing, pumps, reservoirs, monitors, electrocardiogram machines, lights, and anesthesia devices.

12. The medical equipment transfer system of claim 1 wherein the equipment carriage further includes at least one service outlet mounted to the equipment carriage, the service outlet being in communication with a connector, the connector operably connecting the service outlet to a service supply mounted to the first base when the first locking assembly is engaged.

13. The medical equipment transfer system of claim 12 further comprising an indicator light mounted to the equipment carriage to indicate the availability of service through the service outlet.

14. The medical equipment transfer system of claim 12 wherein the service outlet is configured to provide a service selected from the group consisting of water, gas, electricity, and vacuum.

* * * * *